United States Patent
Termanini et al.

(10) Patent No.: US 10,751,198 B2
(45) Date of Patent: Aug. 25, 2020

(54) TOOL AND METHOD FOR REMOVING AN ACETABULAR BALL FROM AN ACETABULAR CUP IN A HIP REPLACEMENT PROSTHESIS

(71) Applicant: HIP INNOVATION TECHNOLOGY, LLC, Boca Raton, FL (US)

(72) Inventors: Zafer Termanini, Port Saint Lucie, FL (US); Brian Vanhiel, Smyrna, GA (US); Linda Braddon, Canton, GA (US)

(73) Assignee: HIP INNOVATION TECHNOLOGY, LLC, Boca Raton, FL (US)

( * ) Notice: Subject to any disclaimer, the term of this patent is extended or adjusted under 35 U.S.C. 154(b) by 114 days.

(21) Appl. No.: 15/742,208

(22) PCT Filed: Jul. 15, 2016

(86) PCT No.: PCT/US2016/042430
§ 371 (c)(1),
(2) Date: Jan. 5, 2018

(87) PCT Pub. No.: WO2017/019327
PCT Pub. Date: Feb. 2, 2017

(65) Prior Publication Data
US 2019/0151117 A1      May 23, 2019

Related U.S. Application Data

(60) Provisional application No. 62/197,200, filed on Jul. 27, 2015.

(51) Int. Cl.
*A61F 2/46* (2006.01)
*A61F 2/34* (2006.01)
*A61F 2/30* (2006.01)

(52) U.S. Cl.
CPC .......... *A61F 2/4637* (2013.01); *A61F 2/4609* (2013.01); *A61F 2002/30649* (2013.01);
(Continued)

(58) Field of Classification Search
CPC .................. A61F 2/4637; A61F 2/4609; A61F 2002/30649; A61F 2002/4627; A61F 2002/4641
See application file for complete search history.

(56) References Cited

U.S. PATENT DOCUMENTS

| | | | |
|---|---|---|---|
| 4,222,382 A | 9/1980 | Antonsson et al. | |
| 4,642,121 A | 2/1987 | Keller | |

(Continued)

FOREIGN PATENT DOCUMENTS

| | | |
|---|---|---|
| CN | 202313816 U | 7/2012 |
| FR | 2926212 A1 | 7/2009 |

OTHER PUBLICATIONS

European Search Report for corresponding application EP16831034.0 dated Mar. 22, 2019.

(Continued)

*Primary Examiner* — Christopher D. Prone
*Assistant Examiner* — Christine L Nelson
(74) *Attorney, Agent, or Firm* — Norris McLaughlin, PA

(57) ABSTRACT

A surgical tool for extracting an acetabular ball from an acetabular cup in an implanted hip prosthesis wherein the acetabular ball is affixed by means of a Morse taper to a stem extending from bottom of the concave portion of the acetabular cup. The surgical tool enables a surgeon to remove the ball without pulling on the acetabular cup and without disrupting any bone ingrowth because the tool maintains pressure on the cup while exerting an opposing pressure pulling on the ball.

6 Claims, 4 Drawing Sheets

STEP 1

(52) U.S. Cl.
CPC ............... *A61F 2002/3483* (2013.01); *A61F 2002/4627* (2013.01); *A61F 2002/4641* (2013.01)

(56) References Cited

U.S. PATENT DOCUMENTS

| | | | |
|---|---|---|---|
| 4,877,020 A * | 10/1989 | Vich | ............... A61B 17/28 606/86 R |
| 5,938,701 A | 8/1999 | Hiernard et al. | |
| 6,132,469 A | 10/2000 | Schroeder | |
| 8,992,627 B2 | 3/2015 | Termanini | |
| 9,248,021 B1 | 2/2016 | Termanini | |
| 2007/0010825 A1 | 1/2007 | Leisinger et al. | |
| 2007/0084012 A1 * | 4/2007 | Savard | ............... E05D 13/1261 16/197 |
| 2019/0151117 A1 | 5/2019 | Termanini et al. | |

OTHER PUBLICATIONS

International Search Report for corresponding application PCT/US2016/042430 dated Sep. 22, 2016.
Written Opinion of the International Searching Authority for corresponding application PCT/US2016/042430 dated Sep. 22, 2016.

* cited by examiner

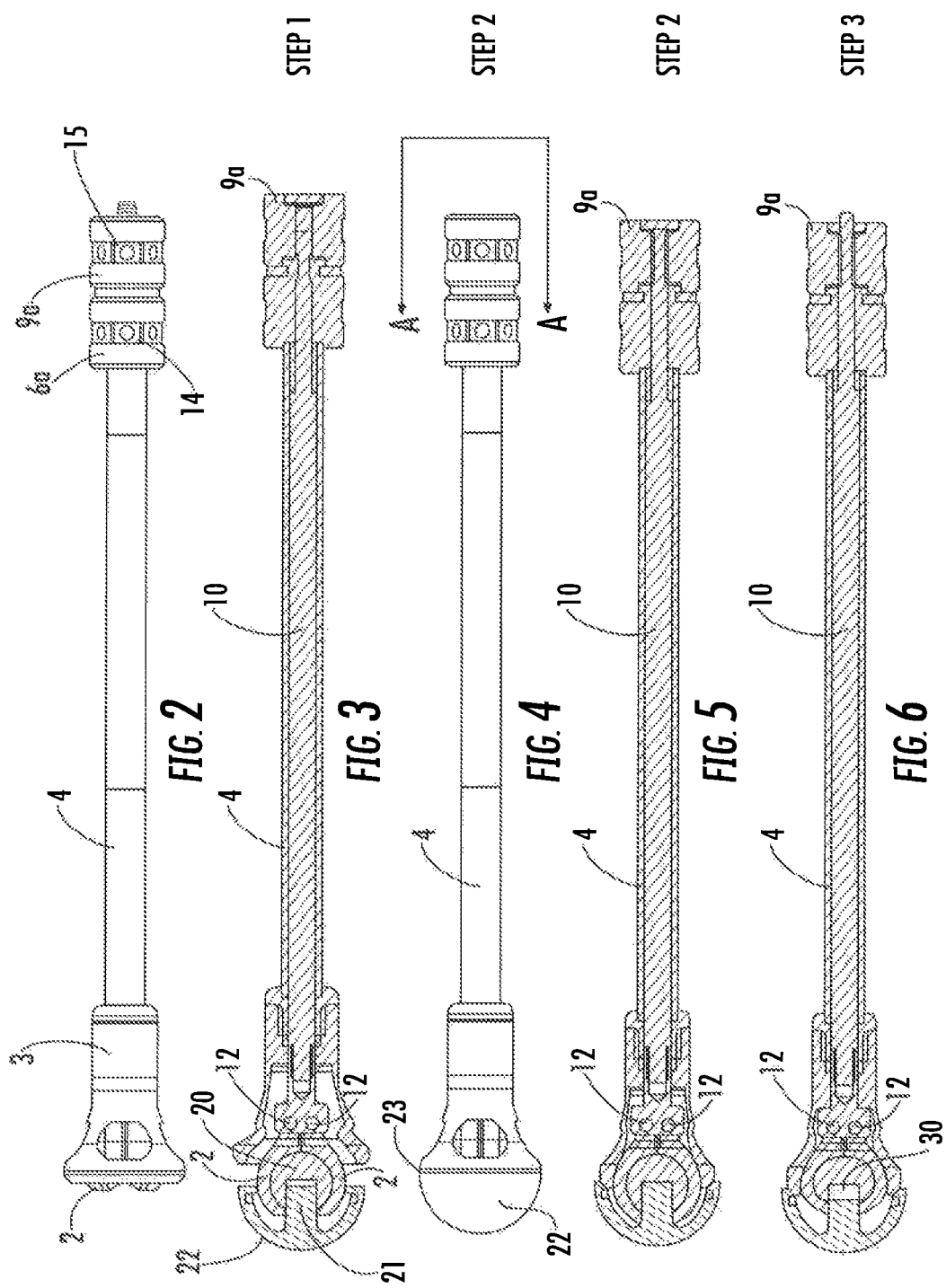

TOOL AND METHOD FOR REMOVING AN ACETABULAR BALL FROM AN ACETABULAR CUP IN A HIP REPLACEMENT PROSTHESIS

This is an application filed under 35 USC 371 based on PCT/US2016/042430 filed 15 Jul. 2016, which in turn claims priority to U.S. Ser. No. 62/197,200 filed 27 Jul. 2015. The present application claims the full priority benefit of these prior applications and herein incorporates by reference the full disclosures of these prior applications as if set forth herein.

BACKGROUND OF THE INVENTION

Field of the Invention

The present invention relates to surgical tools used in connection with a reverse hip prosthesis. More particularly, the invention has to do with a surgical tool for extracting an acetabular ball from an acetabular cup.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, the acetabular ball is affixed by means of a Morse taper to an acetabular cup stem. The stem extends from the bottom of a concave surface of the acetabular cup. The surgical tool of the invention enables a surgeon to remove the acetabular ball from an implanted prosthesis without pulling on the acetabular cup and without disrupting any bone ingrowth. In the present disclosure, we use the term "acetabular ball extractor" from time to time to describe the tool of the invention and the term "tool" or "instrument" is sometimes used to refer to either or both of the first and second embodiments of the invention.

BRIEF DESCRIPTION OF THE DRAWINGS

FIG. 2 is an elevation view of a second embodiment of the tool.

FIG. 3 is a section view of the tool in a first step illustrating the jaws positioned over an acetabular ball which has been affixed in an acetabular cup.

FIG. 4 is an elevation view of the tool in a second step fully engaged with the acetabular ball and cup.

FIG. 5 is a section view of FIG. 4 taken along section line A-A.

FIG. 6 is a section view of the tool in a third step illustrating an acetabular ball separated from the stem of the acetabular cup.

DESCRIPTION OF THE PREFERRED EMBODIMENTS

Figure 1:
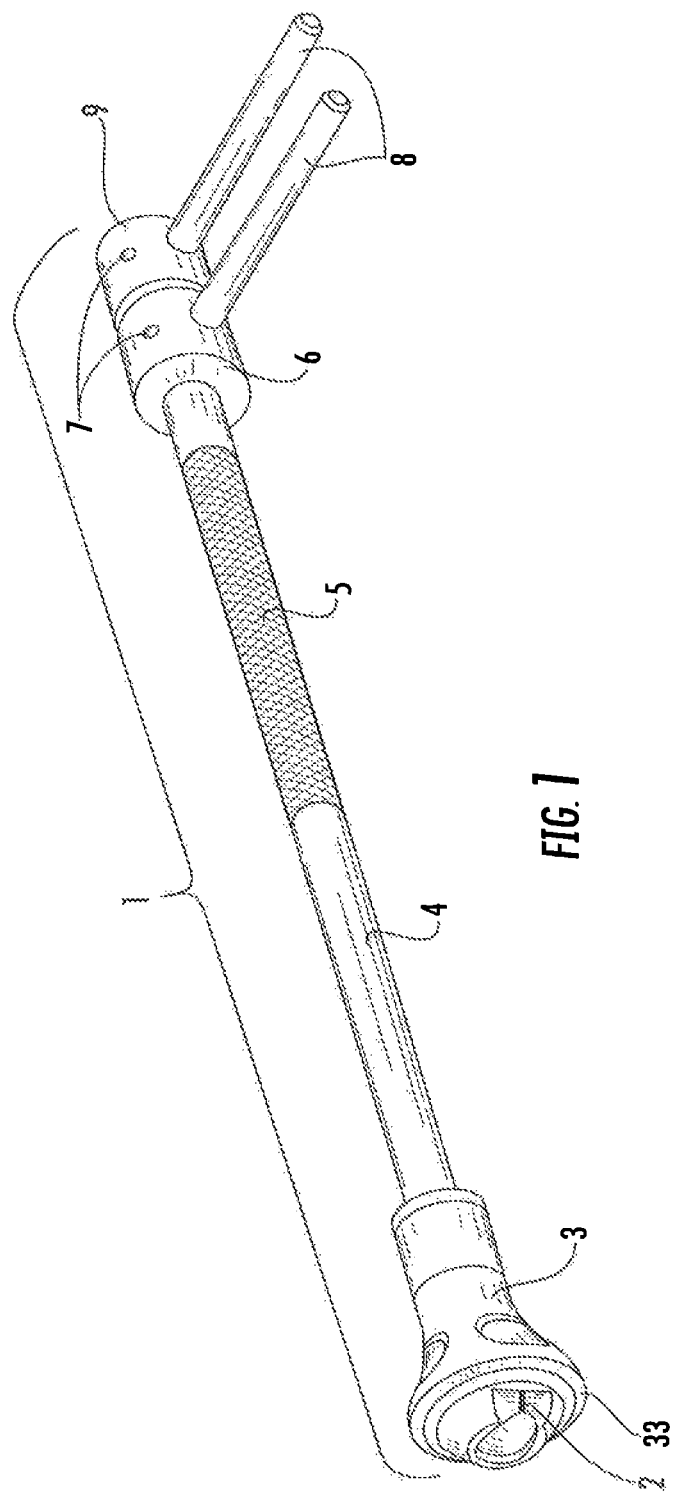
FIG. 1 is a perspective view of a first embodiment of the surgical tool of the invention.

The tool 1 is the first embodiment of the tool of the invention and is illustrated in perspective in FIG. 1. The tool 1a is the second embodiment of the tool of the invention and is illustrated in a partially exploded view in FIG. 12 and in elevation in FIG. 2.

Figure 8:
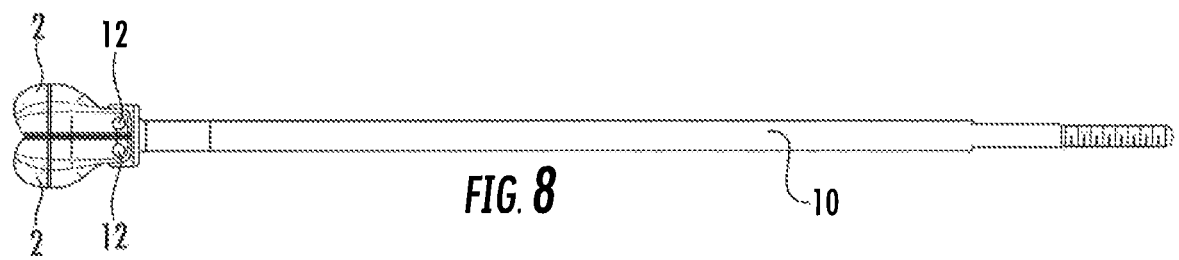
FIG. 8 is an elevation view of a jaw assembly of the acetabular ball extractor.

Referring to FIGS. 1-6, the tool 1 comprises a jaw shaft 10 having two or more than two jaws 2 disposed at the distal end thereof. Each jaw 2 is pivotable about a pin 12 having an axis perpendicular to a central axis of jaw shaft 10. And jaw shaft 10 has a threaded proximal end 11. (See FIGS. 8, 12 and 12A.) The jaw shaft 10 is disposed concentrically in outer shaft 4. A bell shaped element, referred to herein as handle bell 3, is affixed to the distal end of outer shaft 4. The handle bell 3 is internally sized to cause jaws 2 to close as the jaws 2 are drawn into the handle bell 3 by proximal movement of jaw shaft 10 toward the proximal end of the tool 1 as explained in more detail below. The handle bell 3 has a circumferential bell edge 33 at its distal end sized to engage a circumferential cup edge 23 of an acetabular cup. Outer shaft 4 has an optional knurled portion 5.

Figure 7:
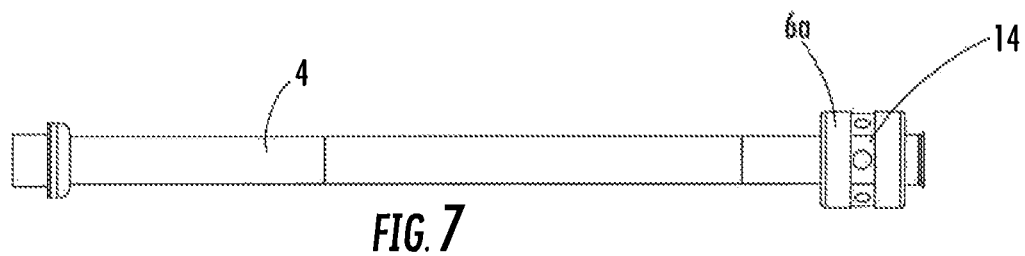
FIG. 7 is an elevation view of a handle or outer shaft for the acetabular ball extractor.
Figure 9:
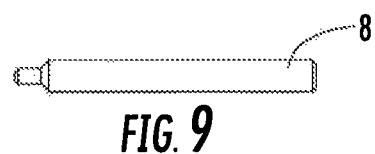
FIG. 9 is an elevation view of a block bar of the acetabular ball extractor.
Figure 10:
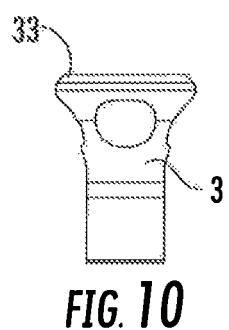
FIG. 10 is an elevation view of the handle bell of the acetabular ball extractor.
Figure 11:
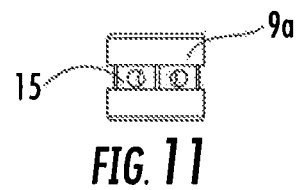
FIG. 11 is an elevation view of a shaft nut of the second embodiment of the acetabular ball extractor.
Figures 12, 12A:
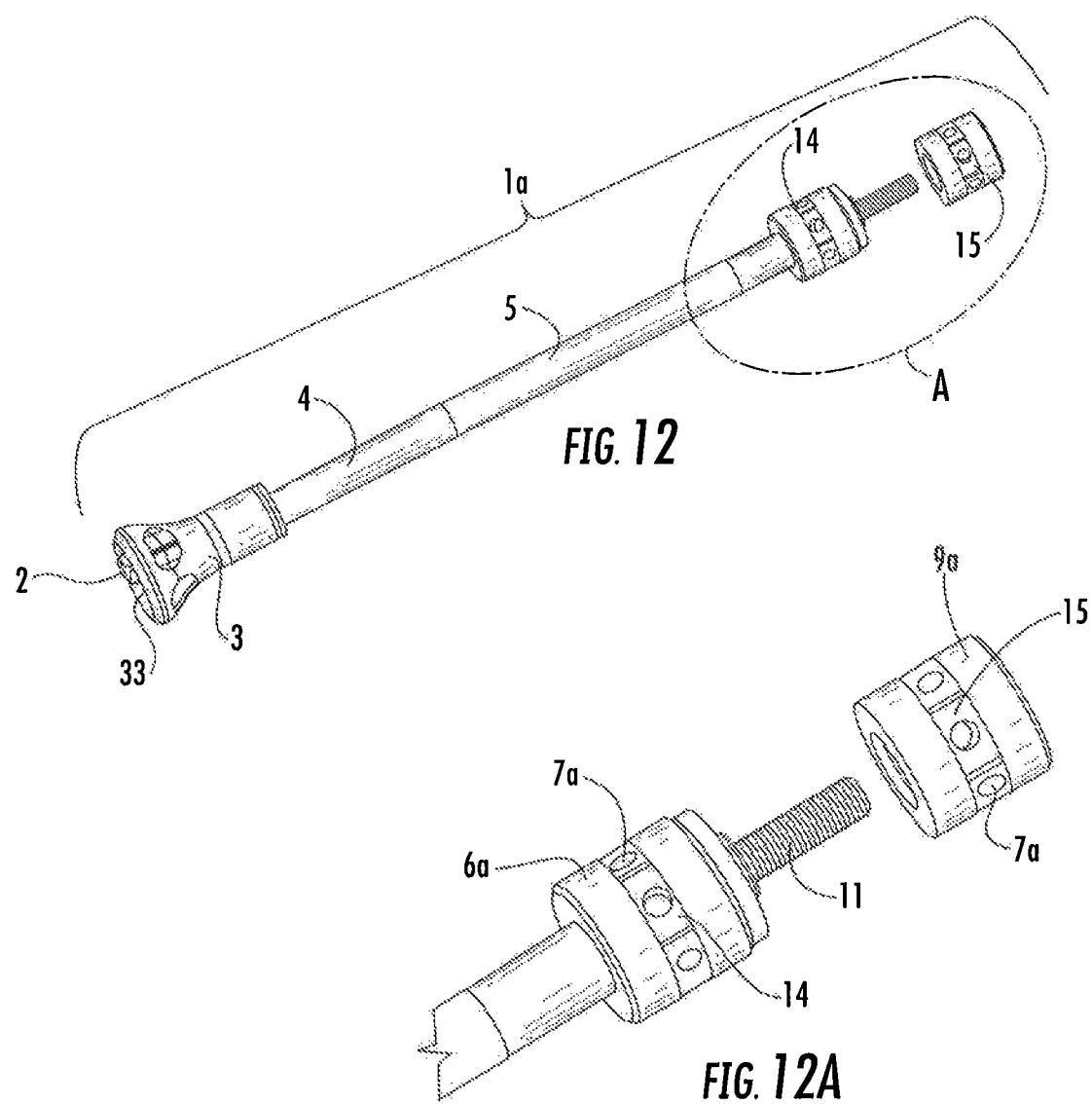
FIG. 12 is a partially exploded view of the second embodiment of the tool of the invention.
FIG. 12A is a magnified view of the proximal end of FIG. 12.

A jaw shaft nut 9 or 9a is threaded onto the proximal end of jaw shaft 10 and an outer shaft nut 6 or 6a is affixed to the proximal end of outer shaft 4. When the jaw shaft nut abuts the outer shaft nut and the threads at the proximal end of shaft 4 are right handed, tightening jaw shaft nut 9 or 9a by turning it in a clockwise (or right-handed) direction will exert a distal force on nut 6 or 6a causing the jaw shaft 10 to move in a proximal direction relative to the outer shaft 4. By way of further explanation, the nuts are disposed adjacent to one another with the jaw shaft nut 9 or 9a being disposed proximally to the outer shaft nut 6 or 6a. Jaw shaft 10 is illustrated in section in FIGS. 3, 5 and 6, and in elevation in FIG. 8. FIGS. 12 and 12A illustrate the threaded proximal end 11 of jaw shaft 10; FIG. 12A being a magnified view of the proximal end A of the tool illustrated in FIG. 12. FIG. 7 is an elevation view of outer shaft 4 with an outer shaft nut 6a thereon. The jaw shaft 10 is illustrated in elevation in FIG. 8 with jaws 2 thereon and a block bar 8 is illustrated in elevation in FIG. 9. FIGS. 10 and 11 are elevations of handle bell 3 and jaw shaft nut 9a, respectively.

The difference between tools 1 and 1a has to do with differences in outer shaft nuts 6 and 6a and jaw shaft nuts 9 and 9a. Nuts 6 and 9 are knurled and holes 7 are provided in the knurled portions to receive block bars 8 which are used to provide leverage in the operation of the tool. Nuts 6a and 9a are also knurled but they are additionally provided with hex portions 14 and 15, respectively. Holes 7a are provided for block bars 8 in hex portions 14 and 15. The hex portions allow the surgeon to use a wrench or wrenches (not shown) instead of some or all of the block bars in order to obtain increased leverage during operation of the tool. Of course, flattened portions on the outer surface of the nuts having shapes other than a hex can be used to permit use of a wrench or other tool in order to obtain increased leverage as will be apparent to those having ordinary skill in the art.

The operation of the tool is illustrated in FIGS. 3-6. The jaws 2 are allowed to open when jaw shaft 10 is pushed in a distal direction while holding shaft 4 so that the jaws move out of handle bell 3. The jaws 2 are hinged by pins 12. In FIG. 3 the jaws 2 are shown in section after they have been pushed out of handle bell 3 and pushed over acetabular ball 20. Two or more than two jaws may be used as will be apparent to those having skill in the art. Acetabular ball 20 is securely affixed by means of a Morse taper on stem 21. Stem 21 is affixed to and extends from the concave surface off acetabular cup 22.

In FIGS. 4 and 5 the circumferential bell edge 33 at the distal end of handle bell 3 has been pushed into engagement with the circumferential cup edge 23 of acetabular cup 22. When the tool has been engaged with the ball and cup in this manner, the next step is to grip shaft 4 while turning jaw shaft nut 9 or 9a causing the jaw shaft to move in a proximal direction so that jaws 2 pull on acetabular ball 20 while handle bell 3 exerts an opposing force on the circumferential cup edge 23 of acetabular cup 22. The opposing force prevents pulling on acetabular cup 22 so that the cup is not pulled out of the acetabulum. A rod or block bar 8 is placed in a hole 7 or 7a of outer shaft nut 6 or 6a and another rod or block bar 8 is placed in a hole 7 or 7a of jaw shaft nut 9 or 9a when additional leverage is needed to exert a pulling force on acetabular ball 20 and an opposing pushing force on acetabular cup 22. The holes 7 and 7a are perpendicular to the central axes of the nuts. If more leverage is needed, the block bars 8 are removed from one or both of shaft nuts 6a or 9a and a wrench is used on either or both shaft nuts by placing the open end of the wrench(es) (not shown) over one or both hex portions 14 or 15. When sufficient force is exerted, the ball separates from stem 21 as illustrated by space 30 in FIG. 6.

The invention claimed is:

1. A surgical tool comprising:

a jaw shaft at least two jaws disposed at a distal end thereof, each jaw having a curved inner surface which at least partially abuts against the generally spherical surface of an acetabular ball affixed by means of a stem extending from a concave surface of an acetabular cup having a circumferential cup edge, each of the jaws being pivotable about an axis perpendicular to a central axis of the jaw shaft and the jaw shaft further having a threaded proximal end;

an outer shaft into which the jaw shaft is concentrically disposed, the outer shaft having a bell shaped handle bell affixed to a distal end thereof, the handle bell having a circumferential bell edge surrounding an opening at a distal end of the handle bell, the circumferential bell edge sized to engage against the circumferential cup edge, the handle bell being internally sized to cause the jaws to close and engage the curved surface of the acetabular ball against at least a part of the curved inner surfaces of the jaws while at the same time the handle bell separates the jaws from the concave surface of the acetabular cup after the jaws are drawn into the handle bell by proximal movement of the jaw shaft toward a proximal end of the surgical tool and, the circumferential bell edge is engaged against the circumferential cup edge of the acetabular cup; and a jaw shaft nut threaded onto the proximal end of the jaw shaft wherein tightening of the nut exerts pressure in a distal direction on the proximal end of the outer shaft causing the jaw shaft to move proximally relative to the outer shaft and thereby causing the jaws to engage the curved inner surfaces of the jaws with the curved surface of the acetabular ball while the jaws exert a pulling force on the acetabular ball while causing the circumferential bell edge of the handle bell to exert an opposing force on the circumferential cup edge of the acetabular cup and to separate the jaws from the concave surface of the acetabular cup, until sufficient tightening of the jaw shaft nut causes the acetabular ball to be released from the stem and the acetabular ball is retained in the jaws until the jaw shaft nut is sufficiently loosened with respect to the jaw shaft to permit for the jaws to release the acetabular ball from within the curved inner surfaces of the jaws.

2. The tool of claim 1 further comprising an outer shaft nut affixed to the proximal end of the outer shaft, the jaw shaft nut and the outer shaft nut being disposed adjacent to one another and the jaw shaft nut being disposed proximally to the outer shaft nut.

3. The tool of claim 2 wherein the jaw shaft nut and the outer shaft nut each further comprise a hole perpendicular to the central axis thereof, each hole being sized to receive a rod wherein the rod provides leverage for turning the jaw shaft nut relative to the outer shaft nut.

4. The tool of claim 3 wherein one or both of the jaw shaft nut and the outer shaft nut further comprise flattened portions on the outer surface thereof to facilitate engagement of a wrench or other tool to provide increased leverage.

5. A method of using the surgical tool of claim 1 comprising the steps of:

disposing the jaws over an acetabular ball which affixed by means of a Morse taper to a stem extending from a concave surface of the acetabular cup and contacting the circumferential bell edge of the bell shaped element with the circumferential cup edge of the acetabular cup and then pulling the jaw stem in the proximal direction while pushing on the acetabular cup in a distal direction until the acetabular ball is released from the stem.

6. The method of claim 5 wherein the jaw stem is pulled in the proximal direction while pushing on the acetabular cup in a distal direction by tightening of the jaw shaft nut.

* * * * *